US007785773B1

(12) United States Patent
Anderson et al.

(10) Patent No.: US 7,785,773 B1

(45) Date of Patent: Aug. 31, 2010

(54) METHOD OF DIAGNOSIS AND KIT THEREFOR

(75) Inventors: David Andrew Anderson, Brunswick (AU); Teresa Sylvia Howard, Malvern East (AU); Anne Healy, Ballincar (IE); Katherine Anders, North Melbourne (AU); Mary Louise Garcia, Fitzroy (AU)

(73) Assignee: Hepgenics Pty Ltd., Malvern (AU)

(*) Notice: Subject to any disclaimer, the term of this patent is extended or adjusted under 35 U.S.C. 154(b) by 317 days.

(21) Appl. No.: 11/604,169

(22) Filed: Nov. 22, 2006

Related U.S. Application Data

(60) Provisional application No. 60/739,317, filed on Nov. 23, 2005.

(51) Int. Cl.
*C12Q 1/70* (2006.01)
*C12N 7/00* (2006.01)
*G01N 33/563* (2006.01)
*G01N 33/533* (2006.01)

(52) U.S. Cl. ........................ 435/5; 435/7.1; 435/235.1; 436/513

(58) Field of Classification Search ........................ None
See application file for complete search history.

(56) References Cited

OTHER PUBLICATIONS

Bishop et al., "Rapid and efficient purification of hepatitis A virus from cell culture", Journal of Virological Methods 47: 203-216, 1994.

MacGregor et al., "Monoclonal Antibodies Against Hepatitis A Virus", Journal of Clinical Microbiology 18(5): 1237-1243, Nov. 1983.

*Primary Examiner*—Mary E Mosher
*Assistant Examiner*—Stuart W Snyder
(74) *Attorney, Agent, or Firm*—Seed IP Law Group PLLC

(57) ABSTRACT

This invention is directed to diagnostic methods detecting the presence of an antibody to a virus in a sample from a subject and kits for using the methods.

19 Claims, 9 Drawing Sheets

SEQUENCE LISTING

```
<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: Adhesive peptide to capture antibody binding
      agent

<400> SEQUENCE: 1

Trp Gly Trp Gln Trp Gly Pro Trp
 1               5


<210> SEQ ID NO 2
<211> LENGTH: 9
<212> TYPE: PRT
<213> ORGANISM: Artificial Sequence
<220> FEATURE:
<223> OTHER INFORMATION: Markush genus of adhesive peptides to capture
      antibody binding agent
<220> FEATURE:
<221> NAME/KEY: VARIANT
<222> LOCATION: 1
<223> OTHER INFORMATION: Xaa = Any Amino Acid
<220> FEATURE:
<221> NAME/KEY: VARIANT
<222> LOCATION: 2
<223> OTHER INFORMATION: Xaa = D or L isomers of Ala, Gly, Ile, Phe,
      Pro, Met, Trp or Val
<220> FEATURE:
<221> NAME/KEY: VARIANT
<222> LOCATION: 3
<223> OTHER INFORMATION: Xaa = Any Amino Acid
<220> FEATURE:
<221> NAME/KEY: VARIANT
<222> LOCATION: 4
<223> OTHER INFORMATION: Xaa = D or L isomers of Ala, Gly, Ile, Phe,
      Pro, Met, Trp or Val
<220> FEATURE:
<221> NAME/KEY: VARIANT
<222> LOCATION: 5
<223> OTHER INFORMATION: Xaa = Any Amino Acid
<220> FEATURE:
<221> NAME/KEY: VARIANT
<222> LOCATION: (6)...(0)
<223> OTHER INFORMATION: Xaa = D or L isomers of Ala, Gly, Ile, Phe,
      Pro, Met, Trp or Val
<220> FEATURE:
<221> NAME/KEY: VARIANT
<222> LOCATION: (7)...(0)
<223> OTHER INFORMATION: Xaa = Any Amino Acid
<220> FEATURE:
<221> NAME/KEY: VARIANT
```

-continued

```
<222> LOCATION: (8)...(0)
<223> OTHER INFORMATION: Xaa = Any Amino Acid
<220> FEATURE:
<221> NAME/KEY: VARIANT
<222> LOCATION: (9)...(0)
<223> OTHER INFORMATION: Xaa = D or L isomers of Ala, Gly, Ile, Phe,
      Pro, Met, Trp or Val

<400> SEQUENCE: 2

Xaa Xaa Xaa Xaa Xaa Xaa Xaa Xaa Xaa
 1               5
```

METHOD OF DIAGNOSIS AND KIT THEREFOR

CROSS-REFERENCE TO RELATED APPLICATION

This application claims the benefit under 35 U.S.C. §119 (e) of U.S. Provisional Patent Application No. 60/740,697 filed Nov. 23, 2005, where this provisional application is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 440078_401_SEQUENCE_LISTING.txt. The text file is 2 KB, was created on Jul. 18, 2008, and is being submitted electronically via EFS-Web.

FIELD OF THE INVENTION

The present invention relates to the field of diagnostics and provides a method for detecting the presence of an antibody to a virus in a sample from a subject. Even more particularly, the present invention provides a kit for diagnosing or monitoring a viral infection by detecting the presence of an antibody to a virus in a test sample from a subject. The invention further relates to an immunographic device and kit that facilitate the rapid diagnosis or monitoring of hepatitis A virus (HAV) infection under a range of conditions such as in laboratory, clinic, home, office, bush and field environments.

BACKGROUND OF THE INVENTION

A diverse range of assays are used in research, analysis, development and clinically to detect analytes of interest. Immunoassays are a particularly useful form of assay that exploit the specificity, strength and diversity of antibody-antigen reactions to analyse samples and detect specific components therein. A wide range of immunoassay techniques are available, such as those described in Wild D. "The Immunoassay Handbook" Nature Publishing Group, 2001.

The detection of antibodies to specific antigens has been used in the diagnosis of specific disease states. For example, the presence of antibody to hepatitis A virus indicates infection with hepatitis A virus and the likelihood of immunity to subsequent infection with that virus. The detection of different class of antibody or immunoglobulin can also provide further information about a disease or a subject's immune status. For example, a current disease state may be distinguished by the presence of IgM antibody while infection in the more distant past may be distinguished by the detection of IgG antibodies.

Methods for the detection of antibody to specific antigens are also known. For example, the enzyme-linked immunosorbent assay (ELISA) and radioimmunoassay (RIA) are routinely used in laboratories. These methods generally require some level of skill in laboratory techniques. A variety of methods have also been developed which require little skill and are rapid to perform, and which are therefore suitable for the detection of antibody to specific antigens at the point of care or analysis. In particular, immunochromatographic or dipstick enzyme-linked immunosorbent kits have been developed to assay for a number of infections including viral infections.

In many immunoassays, it is necessary to form a conjugate containing the specific antigen together with a detectable marker. The antigen of a virus may, for example, be conjugated with colloidal gold such that immune reactivity between the antigen-colloidal gold complex and specific antibody in a device can be detected. Alternatively, the antigen of a virus may be conjugated with an enzyme such as horseradish peroxidase, such that immune reactivity between the antigen-enzyme complex and specific antibody can be detected in an ELISA.

However, the process of conjugation between colloidal gold or enzyme and the antigen of interest may result in a reduction of the immune reactivity between the antigen and the antibody which it is intended to detect. Specifically, the antibody binding site may be the physical site of binding to the colloidal gold or enzyme such that it is inaccessible to the antibody molecule, or the process of binding may alter the conformation of the antigen such that it is no longer recognised by the antibody molecule. At the least, binding of the antigen to colloidal gold or enzyme may be in a random orientation, such that only a proportion of the antigen molecules are available to react with patient antibody to give a detectable signal in a diagnostic test.

The preparation of gold or enzyme conjugates with antigen requires the use of highly purified antigens to prevent the formation of gold or enzyme conjugates containing contaminating proteins which could then react with antibody resulting in non-specific reactions and unreliable test results. The processes used for extensive purification of antigens add to the cost of such preparations, and may also result in a reduction of immune reactivity of the antigen.

Viral particles, albeit with some notable exceptions, are typically roughly spherical and about 30 to 100 nm in diameter. Viral Hepatitis may be caused by one or more viruses such as hepatitis A virus (HAV), hepatitis B virus (HBV), hepatitis C virus (HCV), hepatitis D virus (HDV), hepatitis E virus (HEV) and hepatitis non A-E virus (HNAEV). Chronic liver disease is frequently caused by Hepatitis B, C or D. HAV is a highly contagious virus which infects the liver and causes flu-like symptoms and liver damage. It is the most common form of hepatitis being transmitted through ingestion of contaminated faeces and currently is thought to have infected at least 2 billion people or 40 million people across the world each year, assuming they are infected over a 50 year period. HAV is diagnosed in the laboratory setting by detecting IgM antibodies to antigens from HAV.

Despite the existence of a wide range of immunoassays for detecting patient antibodies to specific antigens, the practical limitations of adapting these assays to a format suitable for use with viral antigens and antibodies determined thereby in the general population and to a format suitable for use in environments without access to laboratory equipment or suitably trained operators has hitherto prevented the successful development of a diagnostic kit for hepatitis A virus which provides robust, rapid and accurate diagnosis of infection even away from the laboratory or clinic.

RELATED REFERENCES

PCT Published Patent Application WO 2005/045439 discloses a detection complex which is reported to be useful for detecting a specific analyte of interest in a sample. The disclosure of this application is incorporated in full by reference herein.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Accordingly, in one embodiment the present invention provides a method for diagnosing or monitoring an infection with a virus by detecting the presence of an antibody to the virus in a test sample from a subject, the method comprising (a) applying a test sample derived from a subject to a sample portion of an immunographic device wherein the sample portion is operably connected to a test portion of the device and wherein components of the test sample flow from the sample portion towards and through the test portion which comprises an antibody binding agent such that substantially only the antibody to the virus in the test sample binds to the antibody binding agent to form a captured antibody. In some embodiments, antibody to be detected, if present, or other antibodies in the sample are captured onto further test or control portions of the chromatographic device.

In some embodiments, the test sample is whole blood. In other embodiments, the sample is a fluid which contains antibodies derived from the body, such as serum or other blood products, plasma, saliva, tears and milk. Blood may, in some embodiments, be maintained in the presence of an anticoagulant such as heparin, sodium citrate or ethylene diamine tetra acetic acid (EDTA).

The immunographic device comprises a porous membrane or material which has a pore size which allows or facilitates capillary flow or diffusion of the components of the method such as virus particle, detection marker, viral particles, detection marker-viral particle complex, and antibody through the material. In some embodiments, the device comprises portions comprising material of different pore size, or non-porous material, the material being contiguous with the first material and designed to receive a sample or receive or store components of the method. In some embodiments, the portions of the immunographic device are separate, contiguous or overlapping and/or designed to come together in use. Portions of the device are "operably connected" or "chromatographically connected" when components of the method such as antibody, detection marker, viral particles, detection marker-viral particle complexes flow from one portion to another by capillary flow or diffusion.

In some embodiments, the sample portion is chromatographically connected to a test portion of the device, the test portion comprising an antibody binding agent such as for example an antibody or an antibody binding fragment thereof. In an illustrative embodiment, the subject is a human and the test portion comprises an anti-human IgM monoclonal antibody which, under the appropriate conditions, recognizes and binds firmly to the Fc portion of human IgM antibodies. Antibodies or antibody binding fragments thereof which recognise one or more class of antibody may be used in one or more test or control portions of the immunographic device. In one preferred embodiment antibodies are bound to a portion of the device using adhesive peptides as described herein. When the test portion comprises anti-species IgM antibodies, these antibodies capture IgM antibodies present in the subject sample. Accordingly, in some embodiments, when chromatographically active components of the subject sample move from the sample portion towards and through the test portion, antibodies of a class determined by the specificity of the antibody binding agent are captured onto test or control portions of the device and the remainder of the sample is uncaptured. This arrangement which is preferred ensures that substantially only the antibody to be detected is allowed to interact with virus particles. In some embodiments, the uncaptured components of the test sample are collected chromatographically into an absorbent sucker portion which is positioned in any orientation with respect to the test portion. Larger particulate components of the subject sample, such as red blood cells or white blood cells which are typically more than about 5 μm in diameter may be retained in the sample portion, for example, by selecting a material for the sample portion of suitable mesh or pore size and/or by the inclusion of specific reagents such as antibodies or lectins to bind and retain these components. For example, monocytes may be retained in the sample portion using anti-CD14 antibodies bound to the material. Anti-glycophorin antibodies may be used to retain/remove red blood cells.

Once the test portion of the immunographic device has been exposed to antibody in the subject sample, the method proceeds by b) allowing contact between a viral particle of the virus stored in a virus portion of the device with a detection marker stored in a conjugate portion of the device under conditions in which the detection marker binds to some but not all binding regions (epitopes) of the viral particle to form a detection marker-viral particle complex.

In some embodiments, the detection marker comprises a visually detectable reporter molecule and a positive result may be essentially immediately observed in the test and/or control portions of the immunographic device. For example, in addition to colloidal gold, as exemplified herein, other colloidal metal or metal oxide particles or colloidal non-metal particles or dyes or coloured latex are conveniently used as visually detectable markers.

In other embodiments, the detection marker may be detected using detectable characteristics of the detection marker and a wide range of detection protocols using detectable markers are well known to those of ordinary skill in the art.

In some embodiments, the detection marker is directly or indirectly bound or otherwise associated with a viral binding agent. In a preferred embodiment, the viral binding agent is an antibody or a viral binding fragment thereof. In some embodiments, the detection marker is connected to the viral binding agent using binding partners known in the art such as without limitation biotin:avidin or anti-biotin antibody:biotin.

The correct ratio of detection marker to viral particle to achieve the desired level of binding is determined by assembling test kits using one or more quantities of virus (for example 1 μl, 0.5 μl per test of virus prepared according to the method described by Bishop et al., *J. Virol. Methods,* 47:203-116, 1994) and detection marker formed by mixing two or more quantities of, for example, gold conjugated to anti-biotin antibody (for example about 2OD, 4OD gold anti-biotin) and a wide range of quantities of biotinylated monoclonal antibody to viral particle (for example about 0.025, 0.05, 0.1, 0.2, 0.4, 0.8 μg/ml). The correct ratio is then obtained by performing tests using each of the devices with a standard sample containing antibody to the viral particle, with the correct ratio being that which gives the strongest assay signal.

In some embodiments, the method further comprises (c) contacting the detection marker-viral particle complex with the test portion under conditions in which the complex will bind to captured antibody, if present in the test portion, to form a detection marker-viral particle-antibody complex. In the final step, the method comprises d) detecting the presence of the detection marker-viral particle-antibody complex in the test portion. In a preferred embodiment and as shown in the Examples a positive signal is determined simply by observing the detection marker in the test portion of the device In some embodiments, as a positive control, detection marker-viral particle complex is also detected on control portions of the device. For example, in one embodiment wherein the viral binding agent is an antibody, the control portion comprises an antibody binding agent to capture the detection marker-antibody complex and the detection marker-antibody-viral particle complex. In some embodiments, the amount of antibody in the test sample can be quantified by assessing the intensity of signal from the detection marker relative to controls.

In some embodiments, the subject is a human. The present invention extends, however, to primates, livestock animals, laboratory test animals, companion animals and avian species as well as non-mammalian animals such as reptiles. The method has applications, therefore in human, livestock, veterinary and wild-life therapy and diagnosis.

In an illustrative embodiment, the present invention provides a method for diagnosing or monitoring an infection with a hepatitis A virus by detecting the presence of an antibody to the virus in a test sample from a subject, wherein the method comprises:

a) applying the test sample derived from the subject to a sample portion of an immunographic device wherein the sample portion is operably connected to a test portion of the device and wherein components of the test sample flow from the sample portion to and through the test portion which comprises an antibody binding agent such that substantially only the antibody to the virus in the test sample binds to the antibody binding agent to form a captured antibody; and b) contacting a viral particle of the hepatitis A virus stored in a virus portion of the device with a detection marker stored in a conjugate portion of the device under conditions in which the detection marker binds to some but not to all binding regions of the viral particle to form a detection marker-viral particle complex; and c) contacting the detection marker-viral particle complex with the test portion under conditions in which the complex will bind to the captured antibody, if present in the test portion, to form a detection marker-viral particle-antibody complex; and d) detecting the presence of the detection marker-viral particle-antibody complex in the test portion.

In some embodiments, the antibody in the test sample to be detected is total antibody or IgM antibody. In another embodiment, the antibody binding agent in the test portion is an anti-subject species antibody or an antibody binding fragment thereof.

The present invention further provides a kit comprising an immunographic device required to perform the method. Generally, the kit further comprises a set of instructions for using the kit to detect the presence of the antibody to the virus in the test sample. In some embodiments, the presence of antibodies to hepatitis virus in a subject with the signs and symptoms of a hepatitis infection is indicative of infection with the virus. In the exemplified embodiment, for example, the presence of IgM antibodies to hepatitis A virus is indicative of an acute infection with hepatitis A virus. As shown in Table 3, the subject illustrated kit provides a highly specific and sensitive result.

Accordingly, in another aspect, the present invention provides a kit for detecting antibodies determined by a virus particle in a sample from a subject, in compartmental form comprising an immunographic device comprising portions for receiving the sample, portions for receiving or comprising the detection marker and a viral particle, together with test and control portions of the device and wherein substantially only the antibody to be detected comes into contact with the virus particle. In some embodiments, the portions of the device are separate, contiguous or overlapping. In some other embodiments, a suspension or solution comprising the detection marker and a suspension or solution comprising the viral particle contact each other for a brief period prior to contact with the test portion so that the detection marker binds firmly to some but not all binding regions of the viral particle. This embodiments is particularly useful when the same binding region of the viral particle is used by the sample antibody and the detection marker. In some embodiments, the kit uses reverse flow immunochromatography (see for example, FIGS. 1 to 4). In other embodiments, the kit uses lateral flow immunochromatography (see for example FIGS. 5 to 8).

In one embodiment, the present invention provides a kit for diagnosing or monitoring an infection with a virus by detecting the presence of an antibody to the virus in a test sample from a subject, wherein the kit comprises: a) an immunographic device comprising a porous membrane operably connected to a sample portion, a test portion, and optionally a control portion; and further comprising a sucker portion, a virus portion and a conjugate portion; and b) instructions for using the immunographic device to detect the presence of the antibody to the virus in the test sample. In some embodiments any one or more of the sucker portion, the virus portion and the conjugate portion is operably connected to the porous membrane such that components of the kit can move such as by capillary flow or diffusion between potions. In other embodiment, one or more of the sucker portion, the virus portion and the conjugate portion is operably connected to the porous membrane before using the kit or during the use of the kit.

In further embodiments, the test portion comprises an antibody binding agent, the virus portion comprises a viral particle of the virus, and the conjugate portion comprises a detection marker. The antibody binding agent is itself bound to the test portion and is used to immobilise antibodies of interest in the test sample to the test portion. In some embodiments, the antibody binding agent is an antibody or an antibody binding fragment thereof of an antibody. In one exemplified embodiment, the subject is a human and the antibody or fragment captures human IgM antibodies. In other embodiments, the antibody or fragment captures IgG or other classes of antibody. In another embodiment the antibody or fragment captures total human antibodies. In accordance with the subject method, substantially only the antibody to the virus in the test sample is retained in the test portion by binding to the antibody binding agent to form a captured antibody.

The detection marker is preferably a visually detectable reporter molecule. A large number of visually detectable markers are known to those of skill in the art and include, without limitation a colloidal metal, colloidal metal oxide particle, colloidal non-metal particle, a dye and/or coloured latex. In some embodiments, the detection marker is directly or indirectly bound to a virus binding agent. By "directly" is meant that the detection marker and the virus binding agent are bound together without intervening molecules or agents. By "indirectly" is meant that one or more intervening agents are employed to bind the detection marker to the virus binding agent. An example of an intervening molecule or agent is an antibody or protein binding molecule. In one example colloidal gold is conjugated to an anti-biotin antibody which binds to biotin labelled anti-viral particle antibody. Other examples will be apparent to those of skill in the art.

Accordingly, in one contemplated embodiment, the virus binding agent is an antibody or antigen binding fragment thereof that binds to the viral particle. In some embodiments, the antibody or fragment in the conjugate portion and the antibody to the virus in the sample recognize the same epitope on the viral particle. In one embodiment, the epitope is an immunodominant epitope.

In a preferred embodiment the viral particle is a hepatitis viral particle such as a hepatitis A virus (HAV) viral particle. In the case of hepatitis A virus, the antibody or fragment in the conjugate portion is an anti-HAV antibody.

An adhesive peptide is employed in some embodiments to capture the antibody binding agent to the test portion of the device. In some embodiment, the adhesive peptides has the sequence WGWQWGPW (SEQ ID NO:1) or a derivative thereof having the sequence of:

$X_{aa1}$ $A_1$ $X_{aa2}$ $A_2$ $X_{aa3}$ $A_3$ $X_{aa4}$ $X_{aa5}$ $A_4$, (SEQ ID NO:2) or a part thereof wherein:

$X_{aa}$=any amino acid; and $A_1$ to $A_4$ is independently selected from a hydrophobic amino acid selected from Ala, Gly, Ile, Phe, Pro, Met, Trp, Tyr, Val, D or L isomers thereof; or a functional analog thereof, or a functional derivative thereof comprising at least about 20% amino acid sequence similarity thereto. Conveniently, the antibody binding agent is conjugated to the adhesive peptide. The adhesive peptides contemplated in this embodiment are described in International Publication No. WO 2006/056009, which is incorporated herein in its entirety by reference.

In accordance with some aspects of the present invention the presence of the antibody to the virus in the test sample is detected by:

i) applying the test sample from the subject to the sample portion;

ii) contacting the test sample from the sample portion with the test portion under conditions in which substantially only the antibody to the virus in the test sample is retained in the test portion by binding to the antibody binding agent to form a captured antibody;

iii) contacting the detection marker with the viral particle under conditions in which the detection marker binds to some but not to all binding regions of the viral particle to form a detection marker-viral particle complex; and iv) contacting the detection marker-viral particle complex with the captured antibody under conditions in which the detection marker-viral particle complex will bind to the captured antibody in the test portion to form a detection marker-viral particle-captured antibody complex; and v) detecting the presence of the detection marker-viral particle-captured antibody complex in the test portion.

In some embodiments, step iii) comprises applying a buffer or other wetting agent to the conjugate portion, contacting the conjugate portion to the virus portion and contacting a sucker portion to the porous membrane to facilitate flow of detection marker-viral particle complex over the test and optional control portions. Alternatively, in other embodiments, step iii) comprises applying buffer or other wetting agent to the virus portion, contacting the virus portion to the conjugate portion and contacting a sucker portion to the porous membrane to facilitate flow of detection marker-viral particle complex over the test and optional control portions.

DETAILED DESCRIPTION OF THE INVENTION

Figure 1:
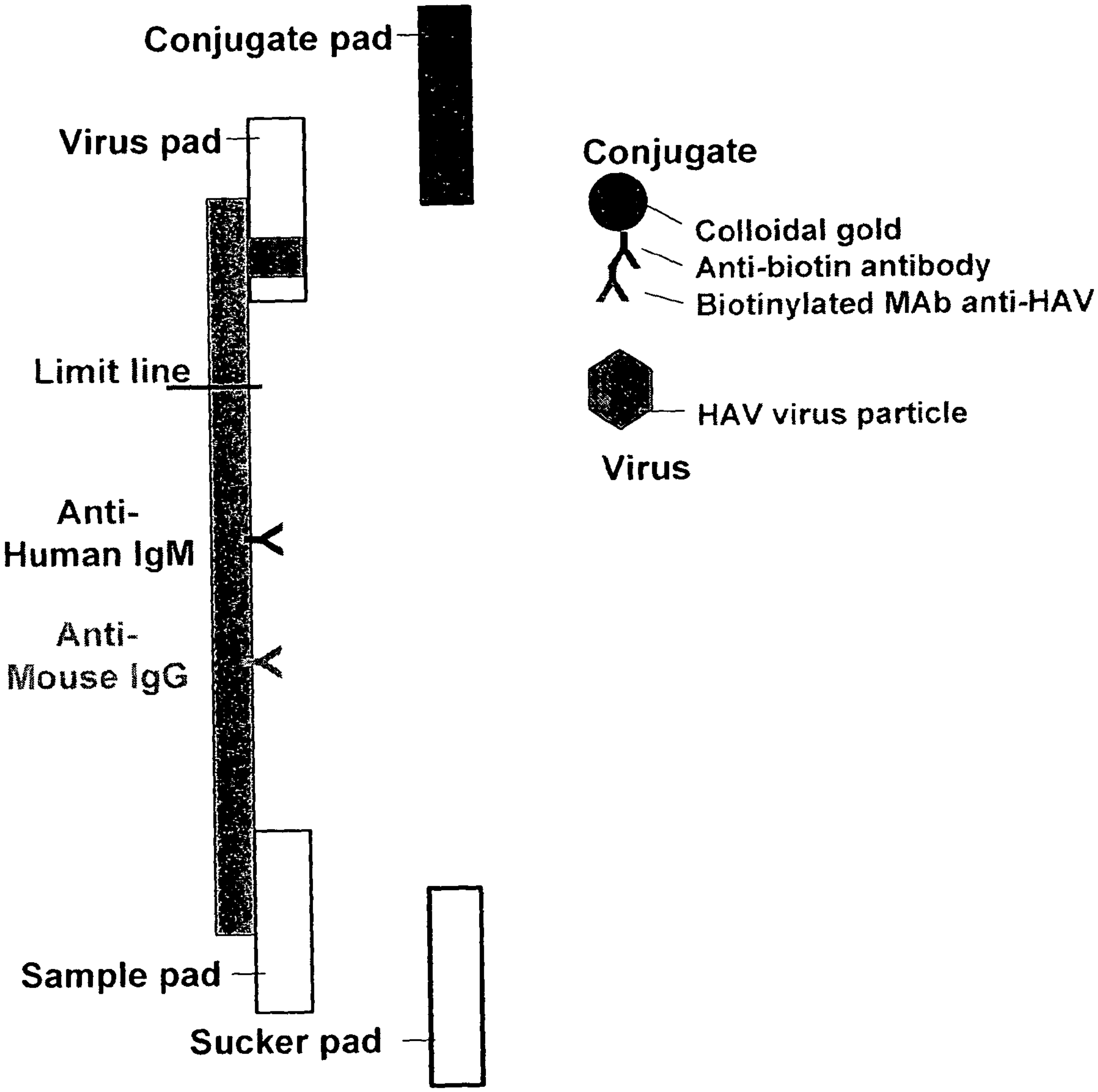
FIG. 1 is a schematic representation of a reverse flow device for detection of IgM anti-HAV antibodies. In this embodiment, a porous membrane (such as nitrocellulose) is prepared by striping a test line consisting of monoclonal antibody to human IgM, a control line consisting of anti-mouse IgG (or other controls), and an inert limit line to provide a guide during assay performance. The nitrocellulose is assembled together with a "virus pad" (virus portion) at one end, consisting of porous material to which has been applied a defined quantity of hepatitis A virus (HAV), and a "sample pad" (sample portion) at the other end, consisting of porous material to which reagents may have been added to trap red blood cells and other extraneous material in the sample. In a separate part of the device, the "conjugate pad" (conjugate portion) consists of porous material to which is applied the conjugate consisting of a detection reagent (such as colloidal gold) conjugated to anti-biotin antibody and complexed with biotinylated monoclonal antibody to HAV, and the "sucker pad" (sucker portion) comprising of an absorbent material. The device is constructed such that the conjugate pad and sucker pad can be brought into contact with the virus pad and sample pad, respectively, during performance of the assay.

The present invention provides a method and a kit for diagnosing or monitoring a viral infection as set forth above in the Summary of the Invention. The method is based on determining the presence of an antibody in a fluid sample from a subject or population of subjects whose viral infection status or immune status relative thereto is unknown or in need of monitoring. Immobilised antibody, essentially free from the remainder of the sample, is detected using a detection marker-viral particle complex. The detection marker and the viral particle are stored in a kit comprising an immunographic device. In some embodiments, separate solutions or suspensions comprising the detection marker and the viral particle are allowed to contact each other under conditions in which such that some but not all of the antibody binding sites on the viral particles are occupied. The present invention has been illustrated in the Examples using hepatitis A virus and the detection of IgM antibodies determined thereby in a human subject.

The articles "a" and "an" are used herein to refer to one or to more than one (i.e. to at least one) of the grammatical objects of the article. By way of example, "an antibody" means one antibody or more than one antibody.

Reference herein to a "chromatographic device" "immunographic device" and the like include a device of any solid, semi-solid, matrix or gel material which is known in the art for facilitating or supporting chromatographic flow or separation. As used herein, the components of the test sample including antibodies, the detection marker, the viral particles, the detection marker-viral particle complexes and components thereof are moved by capillary flow or diffusion through the chromatographic material of the device.

The material of the immunographic device including the various portions may be functionalized or coated to permit for example cross-linking of reagents.

Methods for immobilizing antibodies to solid supports are well known in the art and are described for example in U.S. Pat. No. 4,168,146, Cautrecases *J. Biol. Chem.* 245: 3059, 1970. Materials contemplated for use herein include inorganic materials such as silica, glass, polymeric material such as cellulose, starch, dextrose, agarose, special fibrous paper (filter/chromatography paper) nitrocellulose, cellulose acetate, PVC, polyacrylamide, polysaccharide, polyacrylate, polyethylensulphonate, polyethylene and the like.

"Chromatographically active" components are simply those capable of flow through all or part of the immunochromatographic device.

Reference herein to "derived from" means that the sample is obtained from a particular source but not necessarily directly from that source.

Reference herein to "a virus" or "a virus particle" includes any virus or viral pathogen or a particle of a virus including a virus-like particle. In one embodiment, the viral families contemplated by the present invention are those having a diameter of approximately about 30 to 100 nm. Viral families contemplated for use in the present method and kit include Adenoviridae, African swine fever-like viruses, Arenaviridae, Arterivirus, Astroviridae, Baculoviridae, Birnaviridae, Bunyaviridae, Caliciviridae, Circoviridae, Coronaviridae, Deltavirus, Filoviridae, Flaviviridae, Hepadnaviridae, Hepeviridae, Herpesviridae, Orthomyxoviridae, Paramyxoviridae, Picornaviridae, Poxyviridae, Reoviridae, Retroviridae and Rhabdoviridae.

In some embodiments, the viral particles are the causative agents of hepatitis such as hepatitis A virus (Picornavirus), hepatitis B virus (Hepadnavirus), hepatitis C virus (Flavivirus), hepatitis D virus (Deltavirus) and hepatitis E virus (Hepevirus). In some embodiments, the viral particles are inactivated.

For each of these viruses, the present invention contemplates a kit for diagnosing or monitoring an infection with the virus by detecting the presence of an antibody to the virus in a test sample from a subject, wherein the kit comprises: a) an immunographic device comprising a porous membrane operably connected to a sample portion, a test portion, and optionally a control portion; and further comprising a sucker portion, a virus portion and a conjugate portion; and b) instructions for using the immunographic device to detect the presence of the antibody to the virus in the test sample. In a preferred embodiment, the test portion comprises an antibody binding agent, the virus portion comprises a viral particle of the virus, and the conjugate portion comprises a detection marker. In accordance with the present invention, the presence of the antibody to the virus in the test sample is detected by:

i) applying the test sample from the subject to the sample portion;

ii) contacting the test sample from the sample portion with the test portion under conditions in which substantially only the antibody to the virus in the test sample is retained in the test portion by binding to the antibody binding agent to form a captured antibody;

iii) contacting the detection marker with the viral particle under conditions in which the detection marker binds to some but not to all binding regions of the viral particle to form a detection marker-viral particle complex; and iv) contacting the detection marker-viral particle complex with the captured antibody under conditions in which the detection marker-viral particle complex will bind to the captured antibody in the test portion to form a detection marker-viral particle-captured antibody complex; and v) detecting the presence of the detection marker-viral particle-captured antibody complex in the test portion.

In one illustrative embodiment, the detection marker is colloidal gold conjugated with anti-HAV monoclonal antibody K3-4C8 (MacGregor et al., *J. Clin. Microbiol.,* 18(5): 1237-1243, 1983). The detection marker is added to the conjugate portion of the device, while inactivated HAV viral particle is added to the virus portion and the reagents are then dried. During performance of the assay, the detection marker is rehydrated and then contacts the virus portion allowing rehydration of the virus. In the present invention, the detection marker contacts the viral particle under conditions in which the detection marker binds to some but not to all binding regions of the viral particle to form a detection marker-viral particle complex. In one embodiment, a positive test result is detected by observing a coloured (pink) test portion.

The antibodies contemplated for use in the present invention include immunoglobulin gene products that interact with an antigen i.e., an antigen-binding agent, fragments thereof and non-immunoglobulin gene derived proteinaceous molecules that are capable of serving as an antigen binding agent. The term antibody therefore, includes polyclonal and monoclonal antibodies and parts thereof including Fab portions and antigen-binding determinants. Immunoglobulin genes include κ, λ, α, γ, ($IgG_1$, $IgG_2$, $IgG_3$, $IgG_4$,) δ, ϵ, and μ constant regions and multiple variable region genes.

Typically an immunoglobuling comprises two identical pairs of immunoglobulin chains each pair comprising light chain ($V_L$) and heavy chain ($V_H$) variable portions which have antigen-binding regions. Each pair also comprises a constant region which provide generic antibody functions. Other forms of immunoglobulin are $F_v$, $scF_v$, Fab, $Fab^1$, and $(Fab^1)_2$ forms.

Reference herein to a "class" of an antibody includes reference to any class such as IgM, IgG, IgA etc. By distinguishing between different classes of antibody, it is possible to further define the infection status of a subject and/or its immune status. For example, in relation to hepatitis A virus the detection of IgM in a sample from a subject is indicative that the subject is infected with hepatitis A virus whilst the detection of IgG antibody is indicative of a certain level of immunity thereto.

Combining the separation of antibody class with immunochromatographic flow in the device is particularly efficacious and enhances the utility of the assay.

The ability to rapidly diagnose an infection is important for assessing the ability of a subject to respond to antiviral agents or to mount an immune response to the viral particle. In subjects at risk from infection it is generally important to assess the potential or actual antigen responsiveness in these subjects.

As used herein reference to "detecting" is meant in its broadest sense to include chromatographic assays which qualitatively or quantitatively test for the presence of virus. Chromatographic assays are particularly sophisticated and a large number of different formats are available which are tailored to the prevailing reagents and instruments and the outcomes required in any particular investigation. "Rapid" assays, using chromatographic principles, are tailored for accuracy, speed and ease of use. Immunoassay or enzyme-based chromatographic assays are particularly preferred and these are described in Wild D "The Immunoassay Handbook", Nature Publishing Group, 2001 and by reference to U.S. Pat. Nos. 4,016,043; 4,590,159; 5,266,497; 4,962,023; 5,714,389; 5,877,028, 5,922,537, 6,168,956 and 6,548,309, 6,180,417, and 5,266,497 incorporated herein and information disclosed by references cited therein. Various modifications of immunographic methods are described in Published US Patent Application Nos. 20010006821, 20040087036 and 20040214347 which are incorporated herein in their entirety. Immunogold filtration methods for multiple analyte analyses are described in Published US Patent Application No. 20030165970 incorporated herein by reference.

By "detection marker" is meant a molecule or particle which, by its chemical nature, provides an analytically identifiable signal which allows the detection of antigen bound antibody. As will be well recognised, a wide variety of different reporter systems are available and those allowing rapid visual detection are clearly the most useful in the context of point of care diagnostics.

In some embodiments, the detection marker is a visually detectable reporter molecule such as a colloidal particle or microparticle. Colloidal metal and metalloid particles include those comprising gold, silver, platinum, iron, copper, selenium; metal complexes such as cyclopentadienylmanganese (I) tricarbonyl, gold cluster; and microparticles such as latex and dyed latex particles.

The present invention extends to qualitative or quantitative detection using any of the commonly used reporter molecules in this type of immunoassay such as enzymes, fluorophores or radionuclide containing molecules and chemilluminescent molecules. In the case of an enzyme immunoassay, an enzyme is conjugated to a second antibody generally by means of glutaraldehyde or periodate. Commonly used enzymes include horseradish peroxidase, glucose oxidase, beta galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates which yield a fluorescent product rather than the chromogenic substrates listed above. In all cases, the enzyme labelled antibody is added to the first antibody antigen complex, allowed to bind, and the excess reagent is washed away. A solution containing the appropriate substrate is then added to the complex of antibody-antigen antibody. The substrate will react with the enzyme linked to the second antibody, giving a qualitative visual signal, which may be further quantified, usually spectrophotometrically, to give an indication of the amount of antigen which is present in the sample. Alternatively, fluorescent compounds, such as fluorescein and rhodamine are chemically coupled to antibodies without altering their binding capacity. When activated by a illumination with light of a particular wave length, the fluorochrome labelled antibody absorbs the light energy inducing a state of excitability in the molecule followed by emission of the light at a characteristic wavelength visually detectable with a microscope.

Reference to "antibodies" includes humanised, recombinant, synthetic, hybrid and single chain antibodies. Antibodies may be conveniently prepared and used as described, for example, in Harlow and Lane, "*Antibodies: A Laboratory Manual*" (Cold Spring Harbor Laboratory, 1988). Monoclonal antibodies are conveniently prepared in pure form and in large quantities. The preparation of hybridoma cell lines for monoclonal antibody production by fusing sensitized lymphocytes with an immortal cell line and selecting specific antibody producers is routine in that art as described in Harlow and Lane (supra); and Kohler and Milstein, *European Journal of Immunology,* 6:511-519, 1976.

For the construction of bacteriophage antibody display libraries and lambda phage expression libraries are well known in the art (Kang et al., *Proc. Natl. Acad. Sci. U.S.A.,* 88:4363, 1991; Clackson et al., *Nature,* 352:624, 1991; Lowman et al., *Biochemistry,* 30:10832, 1991; Burton et al., *Proc. Natl. Acad Sci U.S.A.,* 88:10134, 1991; Hoogenboom et al. *Nucleic Acids Res.,* 19:4133, 1991, incorporated herein by reference in their entirety). One particularly advantageous approach has been the use of scFv phage-libraries (Huston et al., *Proc. Natl. Acad. Sci.* 85:5879-5883, 1988; Chaudhary et al., *Proc. Natl. Acad. Sci. U.S.A.,* 87:1066-1070, 1990; Clackson et al., 1991, (supra)). Various embodiments of scFv libraries displayed on bacteriophage coat proteins have been described. Further phage display approaches are also known, for example as described in International Publication Nos. WO 96/06213 and WO 92/01047 (Medical Research Council et al.) and International Publication No. WO 97/08320 (Morphosys) which are incorporated herein by reference.

Human antibody single chain Fv fragments may be cloned and expressed on the surface of, for example, yeast. High affinity scFvs are selected by screening and sorting. High affinity human antibodies are developed using chain shuffling strategies, that is by sequentially replacing the heavy and light chain variable (v) region genes with repertoires of v-genes from unimmunized donors.

Of particular use are display systems, which enable a nucleic acid to be linked to the polypeptide it expresses. Selection protocols for isolating desired members of large libraries are known in the art, as typified by phage display techniques. Such systems, in which diverse peptide sequences are displayed on the surface of filamentous bacteriophage, are useful for creating libraries of antibody fragments (and the nucleotide sequences that encoding them) for the in vitro selection and amplification of specific antibody fragments that bind a target antigen. The nucleotide sequences encoding the $V_H$ and $V_L$ regions are linked to gene fragments which encode leader signals that direct them to the periplasmic space of *E. coli* and the resultant antibody fragments are displayed on the surface of the bacteriophage, typically as fusions to bacteriophage coat proteins (e.g., pIII or pVIII). Alternatively, antibody fragments are displayed externally on lambda phage capsids (phage bodies). An advantage of phage-based display systems is that selected library members can be amplified simply by growing the phage containing the selected library member in bacterial cells. Furthermore, since the nucleotide sequence that encode the polypeptide library member is contained on a phage or phagemid vector, sequencing, expression and subsequent genetic manipulation is relatively straightforward.

In relation to adhesive peptides contemplated for use herein, in some embodiments the adhesive peptides has the sequence WGWQWGPW (SEQ ID NO:1) or a functional derivative thereof having the sequence of:

$X_{aa1}$ $A_1$ $X_{aa2}$ $A_2$ $X_{aa3}$ $A_3$ $X_{aa4}$ $X_{aa5}$ $A_4$, (SEQ ID NO:2) or a part thereof wherein:

$X_{aa}$=any amino acid; and $A_1$ to $A_4$ is independently selected from a hydrophobic amino acid selected from Ala, Gly, Ile, Phe, Pro, Met, Tip, Tyr, Val, D or L isomers thereof; or a functional analog thereof, or a functional derivative thereof comprising at least about 20% amino acid sequence similarity (or identity) thereto.

Conveniently, the antibody binding agent is conjugated to the adhesive peptide. The adhesive peptides contemplated in this embodiment are described in International Publication No. WO 2006/056009 incorporated herein in its entirety by reference.

Specifically, an "amino acid sequence" generally means a sequence of two or more amino acid residues. Adhesive peptides may be less than but about 9 amino acids in length. However, peptides of longer length may be preferred for some applications and the adhesive peptide amino acid sequence may be of any length such as from about 10 to about 50 amino acids or from about 10 to about 1000 amino acids or more. The nine amino acid sequence or a part of this sequence may also be repeated in order to confer enhanced adhesiveness. Further modifications at the N-terminal or C-terminal ends of the peptides including the addition of a few particular amino acids at the N-terminal and any number of amino acids at the C-terminal are expressly contemplated. Thus the amino acid sequence of the adhesive peptide portion of a peptide or polypeptide is generally about 6 to 20 amino acids and the remainder of the molecule may include a proteinaceous or non proteinaceous molecule of any convenient size. The non-adhesive peptide portion of the molecule may be attached by covalent or non-covalent linkage.

As used herein, the term "about" refers to a quantity, level, value, dimension, size, or amount that varies by as much as 30%, 20%, or 10% to a reference quantity, level, value, dimension, size, or amount.

As used herein, the term "alkyl", used either alone or in compound words, denotes saturated straight chain, branched or cyclic hydrocarbon groups, preferably $C_{1-20}$ alkyl, e.g. $C_{1-10}$ or $C_{1-6}$. Examples of straight chain and branched alkyl include, but are not limited to, methyl, ethyl, propyl, isopropyl, butyl, sec-butyl, tert-butyl, n-pentyl and branched isomers thereof, n-hexyl and branched isomers thereof, n-heptyl and branched isomers thereof, n-octyl and branched isomers thereof, n-nonyl and branched isomers thereof, and n-decyl and branched isomers thereof. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

As used herein the term "alkynyl" denotes groups formed from straight chain, branched or cyclic hydrocarbon residues containing at least one carbon-carbon triple bond including ethynically mono-, di- or poly-unsaturated alkyl or cycloalkyl groups as previously defined. The term preferably refers to $C_{2-20}$ alkynyl. Examples include, but are not limited to, ethynyl, 1-propynyl, 2-propynyl, and butynyl isomers, and pentynyl isomers.

As used herein, the term "aryl" denotes a $C_6$-$C_{14}$ aromatic hydrocarbon group. Suitable aryl groups include phenyl, biphenyl, naphthyl, tetrahydronaphthyl, anthracenyl, dihydroanthracenyl and phenanthrenyl. Preferred aryl groups include phenyl, biphenyl and naphthyl.

The term "heterocyclyl" denotes monocyclic, polycyclic or fused, saturated, unsaturated or aromatic hydrocarbon residues, wherein one or more carbon atoms (and where appropriate, hydrogen atoms attached thereto) are replaced by a heteroatom. Suitable heteroatoms include, O, N, S, and Se. Where two or more carbon atoms are replaced, this may be by two or more of the same heteroatom or by different heteroatoms. Suitable examples of heterocyclic groups may include pyrrolidinyl, pyrrolinyl, piperidyl, piperazinyl, morpholino, indolinyl, imidazolidinyl, pyrazolidinyl, thiomorpholino, dioxanyl, tetrahydrofuranyl, tetrahydropyranyl, tetrahydropyrrolyl, pyridyl, thienyl, furyl, pyrrolyl, indolyl, pyridazinyl, pyrazolyl, pyrazinyl, thiazolyl, pyrimidinyl, quinolinyl, isoquinolinyl, benzofuranyl, benzothienyl, purinyl, quinazolinyl, phenazinyl, acridinyl, benzoxazolyl, benzothiazolyl and the like. Preferred heterocyclyl groups include but are not limited to indolinyl, pyridyl, indolyl, quinolinyl, isoquinolinyl and quinazolinyl.

In an illustrative embodiment, $A_1$ to $A_4$ is independently selected from one of Trp, Tyr, Phe, Ala, DY, DW, DF, 60 (L-1-beta-Naphthylalanine), 103 (Beta-(3-Pyridyl)-L-alanine), 161 (Nz-Dabcyl-L-lysine), 264 (beta-(2-quinolyl)-alanine) and 389 (Phenyl-phenylalanine; Biphenylalanine).

"Functional derivatives" of the recited amino acid sequences are also contemplated. These molecules are designed to retain the functional activity (binding) of the reference peptide or to exhibit enhanced activity. "Parts" include fragments comprising from about 50%, 60%, 70%, 80%, 85%, 90%, 95% of the reference sequence. Polypeptide derivatives according to the invention can be identified either rationally, or via established methods of mutagenesis (see, for example, Watson, J. D. et al., "*Molecular Biology of the Gene*", Fourth Edition, Benjamin/Cummings, Menlo Park, Calif., 1987). Random mutagenesis approaches require no a priori information about the sequence that is to be mutated. This approach has the advantage that it assesses the desirability of a particular mutant based on its function, and thus does not require an understanding of how or why the resultant mutant protein has adopted a particular conformation. Indeed, the random mutation of target gene sequences has been one approach used to obtain mutant proteins having desired characteristics (Leatherbarrow R., *J. Prot. Eng.,* 1:7-16, 1986; Knowles J. R., *Science,* 236:1252-1258, 1987; Shaw W. V., *Biochem. J.,* 246:1-17, 1987; Gerit J. A., *Chem. Rev.,* 87:1079-1105, 1987). Alternatively, where a particular sequence alteration is desired, methods of site-directed mutagenesis can be employed. Thus, such methods may be used to selectively alter only those amino acids of the protein that are believed to be important (Craik C. S., *Science.* 228: 291-297, 1985; Cronin et al., *Biochem.,* 27: 4572-4579, 1988; Wilks et al., *Science.* 242:1541-1544, 1988). Peptides or polypeptides, resulting from rational or established methods of mutagenesis or from combinatorial chemistries, may comprise conservative amino acid substitutions. It is well understood in the art that some amino acids may be changed to others with broadly similar properties without changing the nature of the activity of the polypeptide (conservative substitutions).

The terms "sequence similarity" and "sequence identity" as used herein refer to the extent that sequences are identical or functionally or structurally similar on a an amino acid-by-amino acid basis over a window of comparison. Thus, a "percentage of sequence identity", for example, is calculated by comparing two optimally aligned sequences over the window of comparison, determining the number of positions at which the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity which counts as identical, substitutions involving conservative substitutions.

Preferably, the percentage similarity between a particular sequence and a reference sequence (nucleotide or amino acid) is at least about 20% to 40% or at least about 30% to 60% or at least about 70% or at least about 80% or at least about 90% or at least about 95% or above such as at least about 96%, 97%, 98%, 99% or greater. Percentage similarities or identities between 60% and 100% are also contemplated such as 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%.

Functionally equivalent methods and kits employing such methods are clearly within the scope of the invention as described herein.

The present invention is further described by the following non-limiting Examples.

Example 1

A Reverse Flow Device for Detection of IgM anti-HAV

A porous membrane (such as nitrocellulose) is prepared by striping a test line consisting of monoclonal antibody to human IgM, a control line consisting of anti-mouse IgG (or other controls), and an inert limit line to provide a guide during assay performance. The nitrocellulose is assembled together with a "virus pad" at one end, consisting of porous material to which has been applied a defined quantity of hepatitis A virus (HAV, shown in green), and a "sample pad" at the other end, consisting of porous material to which reagents may have been added to trap red blood cells and other extraneous material in the sample. In a separate part of the device, the "conjugate pad" ("detection marker pad") consists of porous material to which is applied the conjugate (shown in brown), consisting of a detection reagent (such as colloidal gold) conjugated to anti-biotin antibody and complexed with biotinylated monoclonal antibody to HAV, and the "sucker pad" comprising of an absorbent material. The device is constructed such that the conjugate pad and sucker pad can be brought into contact with the virus pad and sample pad, respectively, during performance of the assay. A schematic representation is shown in FIG. 1.

Figure 2:
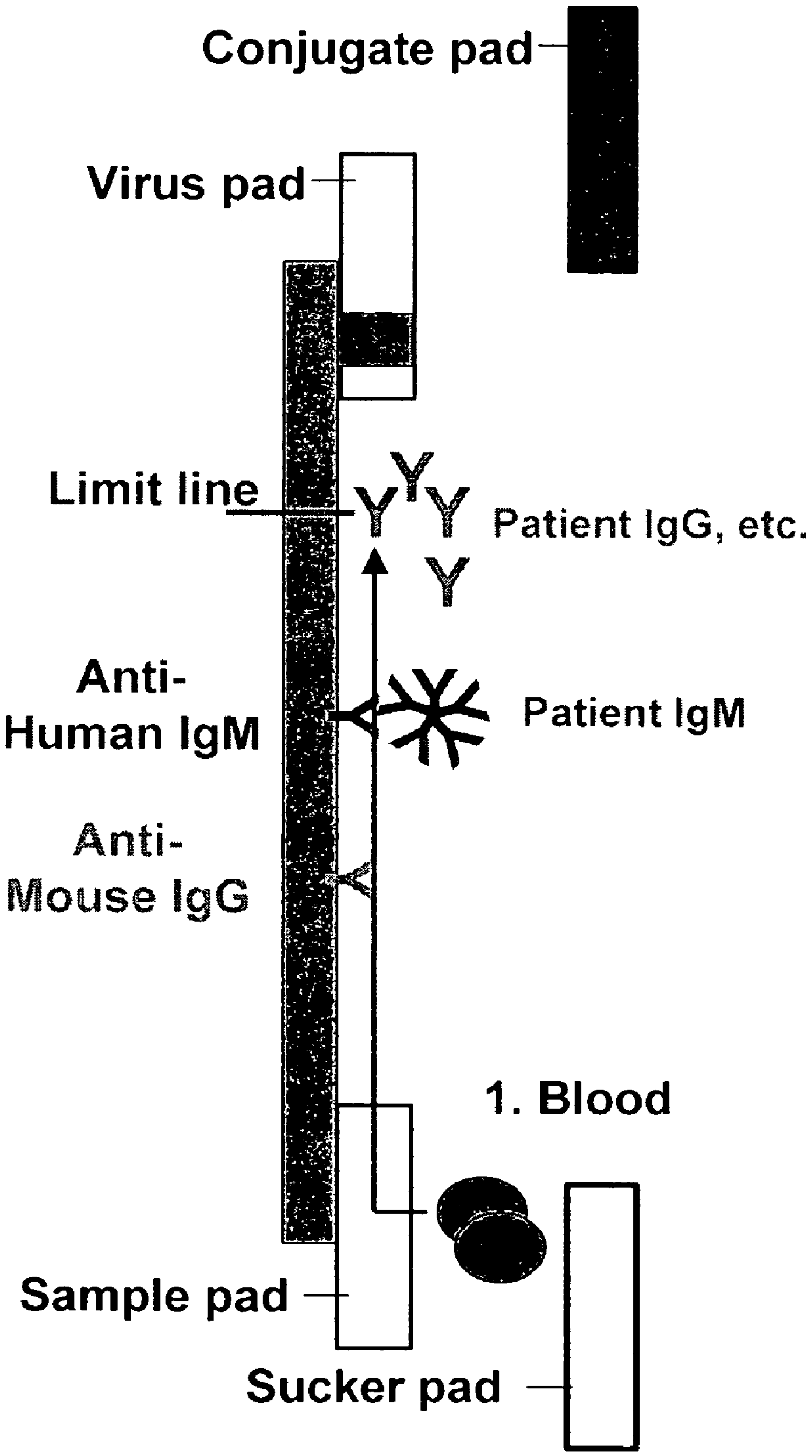
FIG. 2 is a schematic representation of the first step of the reverse flow assay. Specifically, blood or other samples are applied to the sample pad, and the sample flows along the nitrocellulose membrane until it reaches the limit line. A proportion of the IgM present in the sample is captured at the test line (test portion).

In the first step of the reverse flow assay, blood or other samples are applied to the sample pad, and the sample flows along the nitrocellulose membrane until it reaches the limit line. A proportion of the IgM present in the sample is captured at the test line (see FIG. 2).

Figure 3:
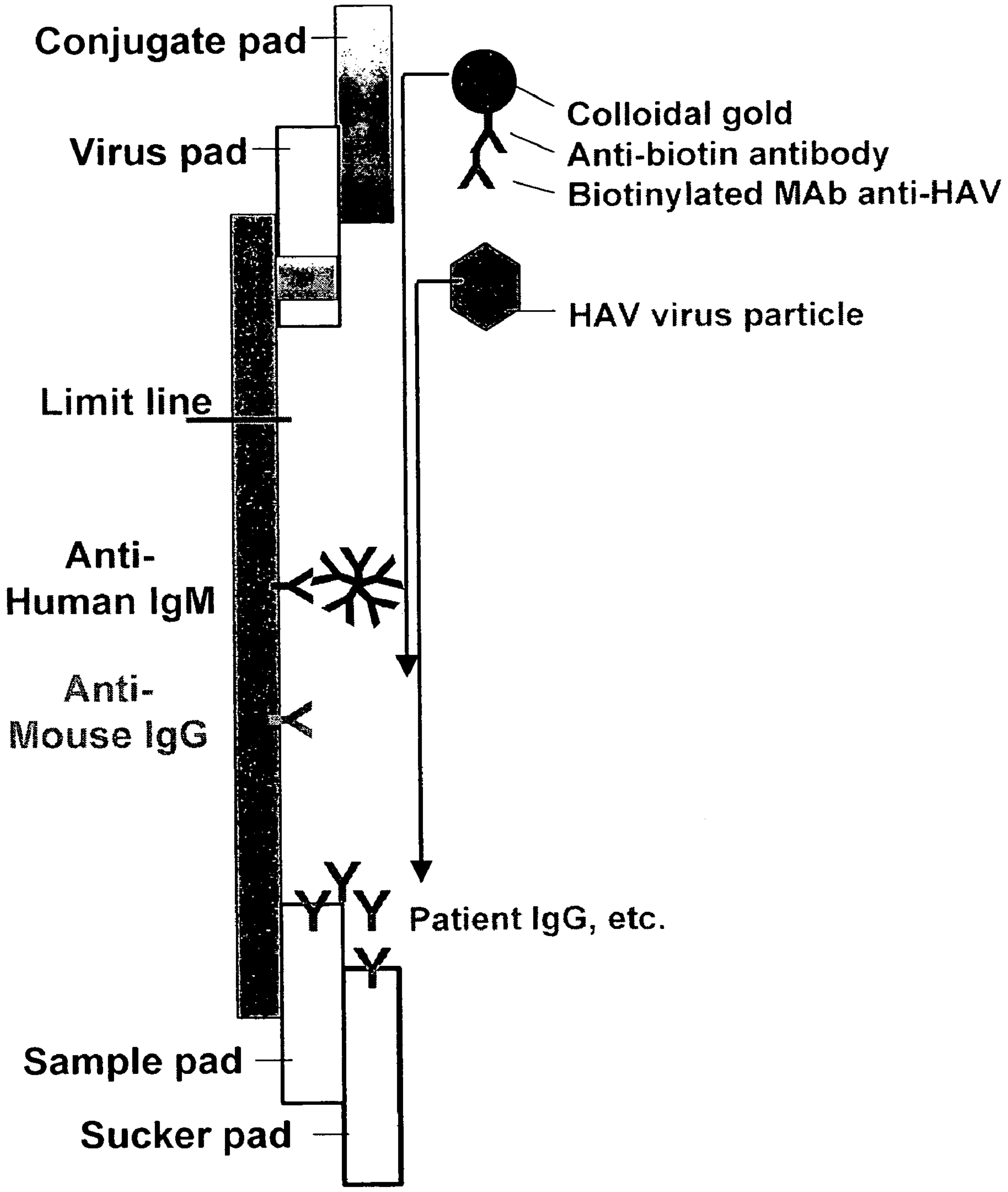
FIG. 3 is a schematic representation of the second step of the reverse flow assay. At the time when the sample front reaches the limit line, the conjugate pad (conjugate portion) and sucker pad (sucker portion) are brought into contact with the virus pad (virus portion) and the sample pad (sample portion), and the flow of reagents and sample is reversed towards the absorbent sucker pad (sucker portion). The conjugate flows through the virus portion, and interacts with the virus for a short time such that only a limited number of the antibody binding sites present on each virus particle are bound by the anti-HAV monoclonal antibody in the conjugate. The virus-conjugate complex flows past the test portion, and any HAV-specific IgM captured in the test portion will result in capture of the virus-conjugate complex also in that portion. Sample contents and excess HAV virus and conjugate will flow past the test portion and control portion, into the absorbent sucker portion.
Figure 4:
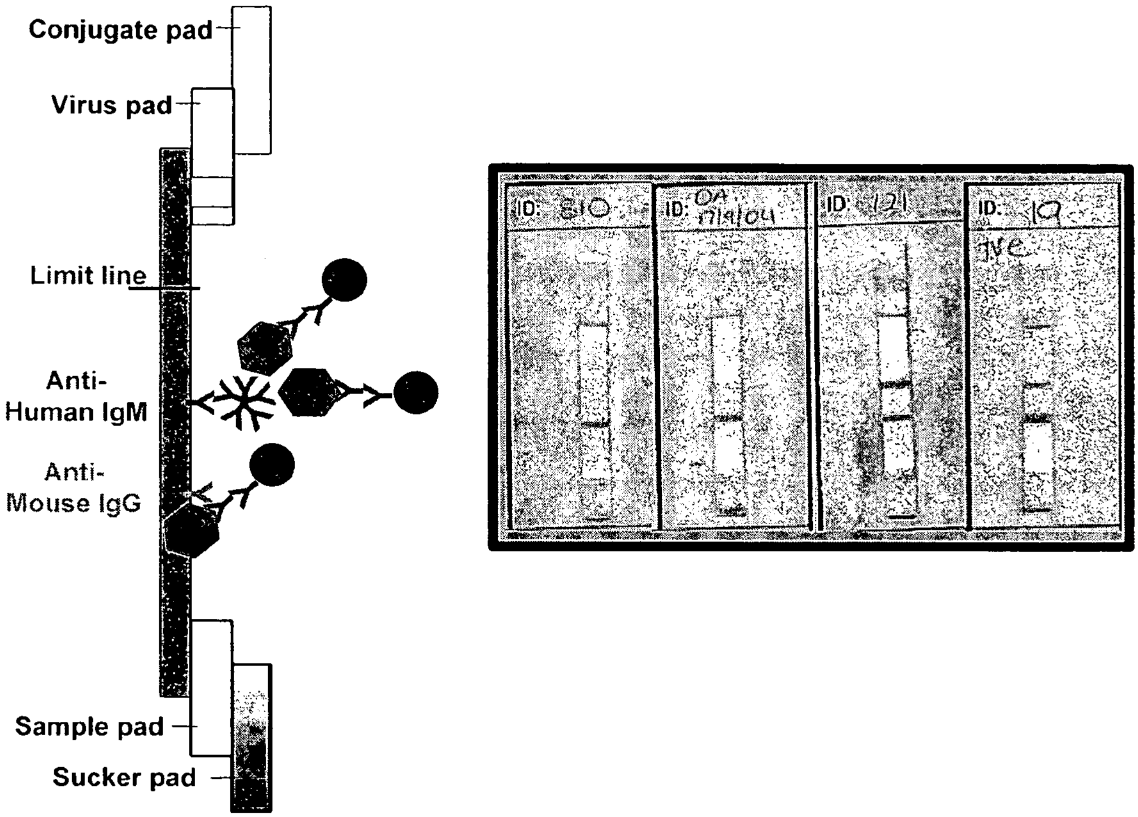
FIG. 4 is a schematic representation of a final result of the reverse flow assay. For example, where the test result is positive for the presence of IgM anti-HAV, such that virus-conjugate complexes are captured at the test line, and virus-conjugate and/or free conjugate is captured at the control line via the interaction of anti-mouse IgG and the monoclonal anti-HAV antibody. Actual results for two positive samples and one negative sample are shown on the right.

When the sample front reaches the limit line, the conjugate pad and sucker pad are brought into contact with the virus pad and the sample pad, and the flow of reagents and sample is reversed towards the absorbent sucker pad. The conjugate flows through the virus pad, and interacts with the virus for a short time such that only a limited number of the antibody binding sites present on each virus particle are bound by the anti-HAV monoclonal antibody in the conjugate. The virus-conjugate complex flows past the test line, and any HAV-specific IgM captured at the test line will result in capture of the virus-conjugate complex also at that line. Sample contents and excess HAV virus and conjugate will flow past the test line and control line, into the absorbent sucker pad (see FIG. 3).

Where the test result is positive for the presence of IgM anti-HAV, such that virus-conjugate complexes are captured at the test line, and virus-conjugate and/or free conjugate is captured at the control line via the interaction of anti-mouse IgG and the monoclonal anti-HAV antibody, two visible lines will be seen (see FIG. 4). Where the test result is negative for the presence of IgM anti-HAV, such that virus-conjugate and/or free conjugate is captured only at the control line via the interaction of anti-mouse IgG and the monoclonal anti-HAV antibody, one visible line will be seen (see FIG. 4). Actual results for two positive samples and one negative sample are shown on the right of FIG. 4.

Example 2

A Lateral Flow Device For Detection of IgM anti-HAV

Figure 5:
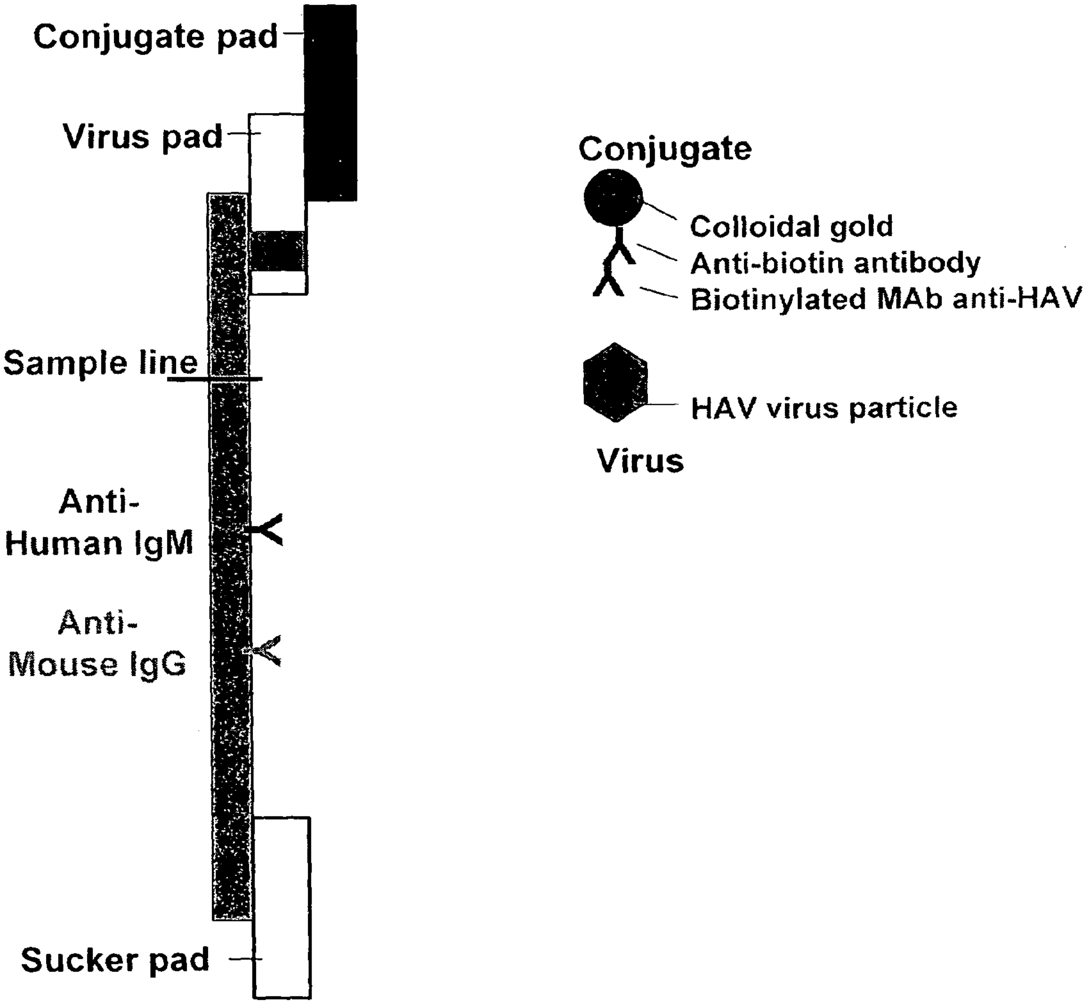
FIG. 5 is a schematic representation showing lateral flow device for detection of IgM anti-HAV. A porous membrane (such as nitrocellulose) is prepared by striping a test portion consisting of monoclonal antibody to human IgM, a control portion consisting of anti-mouse IgG (or other controls), and an inert sample line (or sample pad) to provide a guide for application of the sample during assay performance. This nitrocellulose is assembled together with a "virus pad" and "conjugate (detection marker) pad" at the same end as the sample line, consisting respectively of porous material to which has been applied a defined quantity of hepatitis A virus (HAV), and porous material to which has been applied the conjugate, consisting of a detection reagent (such as colloidal gold) conjugated to anti-biotin antibody and complexed with biotinylated monoclonal antibody to HAV. The nitrocellulose membrane is assembled with an absorbent sucker portion at the other end to the sample portion and virus and conjugate portions.

A porous membrane (such as nitrocellulose) is prepared by striping a test line consisting of monoclonal antibody to human IgM, a control line consisting of anti-mouse IgG (or other controls), and an inert sample line (or sample pad) to provide a guide for application of the sample during assay performance. This nitrocellulose is assembled together with a "virus pad" and "conjugate (detection marker) pad" at the same end as the sample line, consisting respectively of porous material to which has been applied a defined quantity of hepatitis A virus (HAV, shown in green), and porous material to which has been applied the conjugate (shown in brown), consisting of a detection reagent (such as colloidal gold) conjugated to anti-biotin antibody and complexed with biotinylated monoclonal antibody to HAV. The nitrocellulose membrane is assembled with an absorbent sucker pad at the other end to the sample line and virus and conjugate pads. A schematic representation is shown in FIG. 5.

Figure 6:
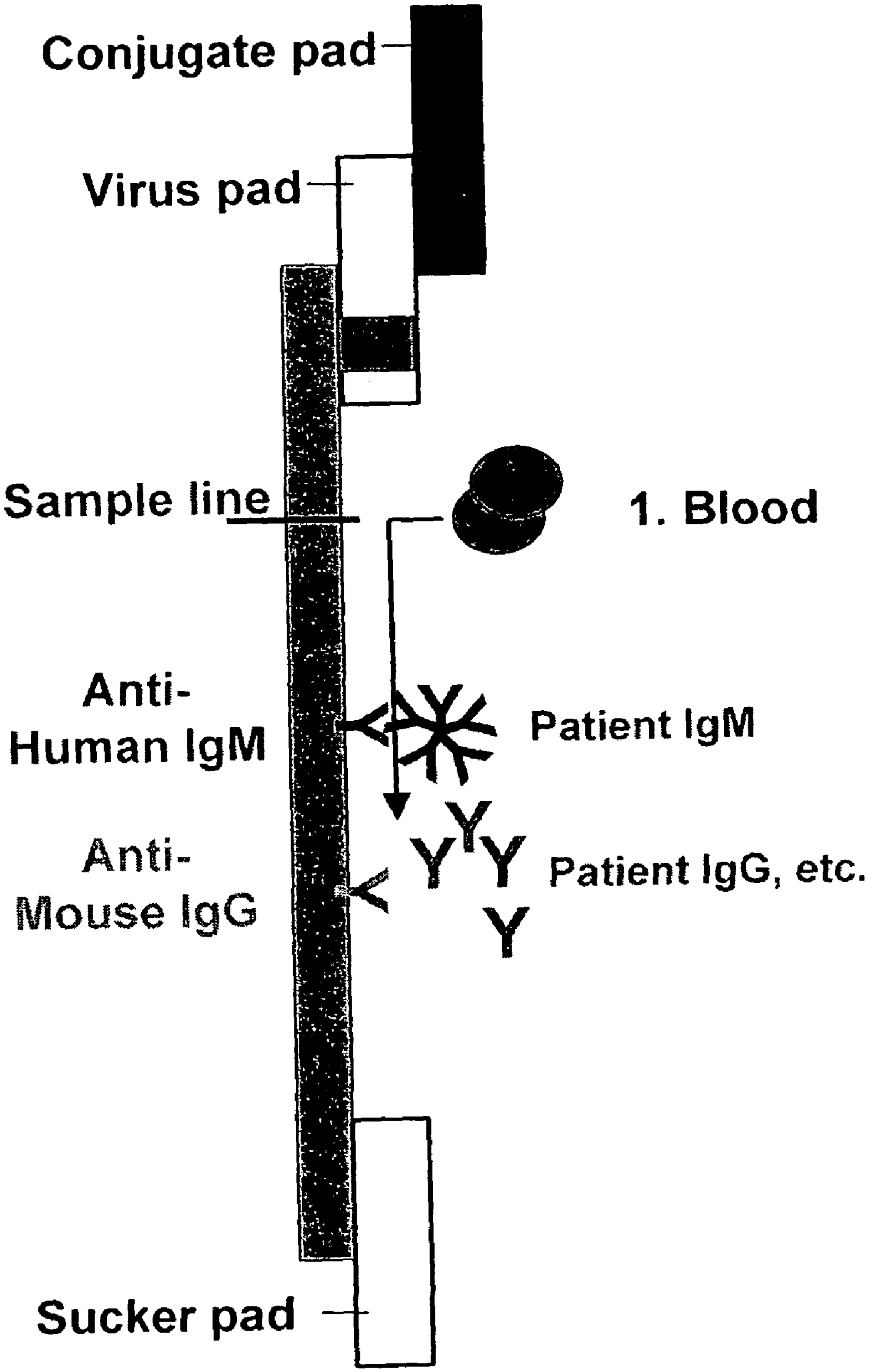
FIG. 6 is a schematic representation of the first step of the lateral flow assay. Blood or other samples are applied to the sample portion/line, and the sample is absorbed into the nitrocellulose membrane and begins to flow. A proportion of the IgM present in the sample is captured at the test line/portion, whereas other sample contents are not captured.

In the first step of the lateral flow assay, blood or other samples are applied to the sample line, and the sample is absorbed into the nitrocellulose membrane and begins to flow. A proportion of the IgM present in the sample is captured at the test line, whereas other sample contents are not captured (see FIG. 6).

Figure 7:
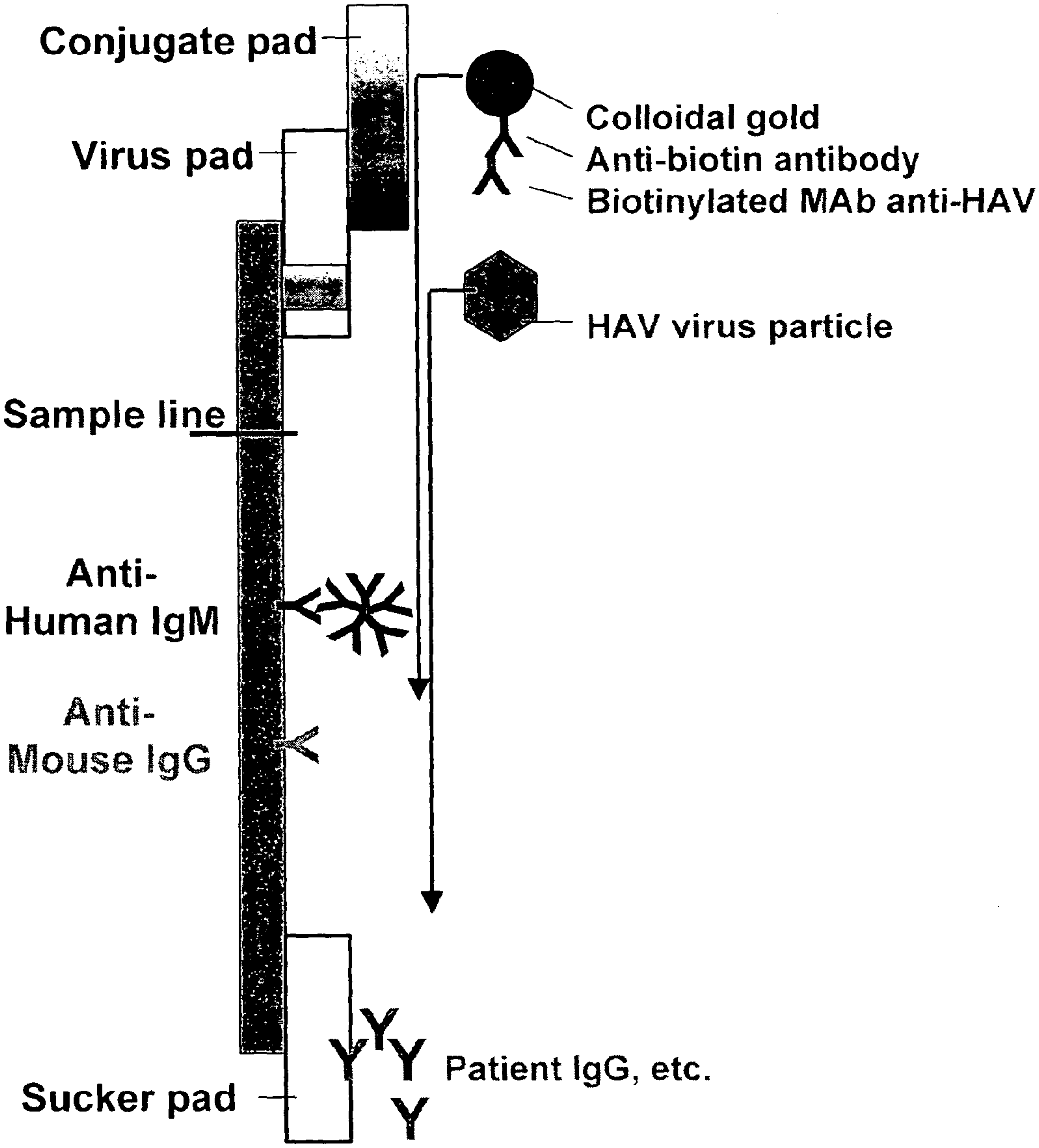
FIG. 7 is a schematic representation of the second step of the lateral flow assay. Buffer is applied to the conjugate pad/portion comprising the detection marker commencing around the time when the sample is fully absorbed into the nitrocellulose, and the flow of reagents and sample is forced towards the absorbent sucker pad/portion. The detection marker flows through the virus pad/portion, and interacts with the viral particle for a short time such that only a limited number of the antibody binding sites present on each virus particle are bound by the anti-HAV monoclonal antibody in the detection marker. The detection marker-viral particle complex flows past the test portion, and any HAV-specific IgM captured at the test portion will result in capture of the detection marker-viral particle complex also at that portion. Sample contents and excess HAV virus and detection marker conjugate will flow past the test line/portion and control portion, into the absorbent sucker portion.
Figure 8:
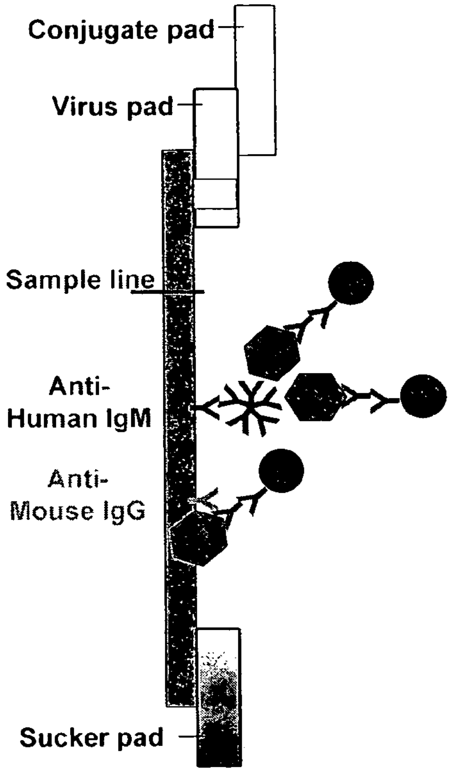
FIG. 8 is a schematic representation of final result of the lateral flow assay. For example, where the test result is positive for the presence of IgM anti-HAV, such that detection marker-virus particle complexes are captured at the test line/portion, and detection marker-virus particle complexes and/or free detection marker (conjugate) is captured at the control portion/line via the interaction of anti-mouse IgG and the monoclonal anti-HAV antibody. Actual results for two positive samples and one negative sample are shown on the right.
Figure 8:
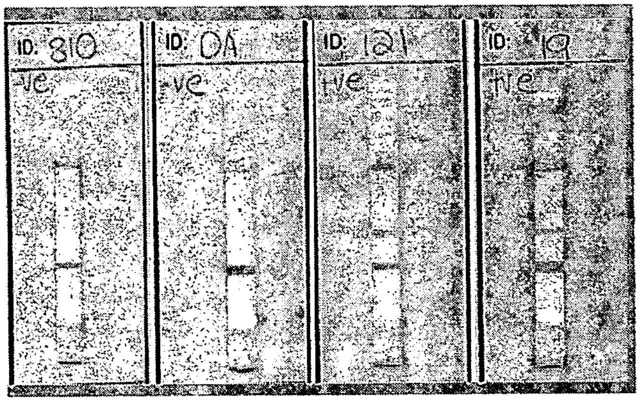

In the next step buffer is applied to the conjugate pad commencing around the time when the sample is fully absorbed into the nitrocellulose, and the flow of reagents and sample is forced towards the absorbent sucker pad. The conjugate flows through the virus pad, and interacts with the virus for a short time such that only a limited number of the antibody binding sites present on each virus particle are bound by the anti-HAV monoclonal antibody in the conjugate. The virus-conjugate (detection marker) complex flows past the test line, and any HAV-specific IgM captured at the test line will result in capture of the virus-conjugate (detection marker) complex also at that line. Sample contents and excess HAV virus and detection marker conjugate will flow past the test line and control line, into the absorbent sucker pad (see FIG. 7).

Where the test result is positive for the presence of IgM anti-HAV, such that virus-conjugate complexes are captured at the test line, and virus-conjugate and/or free conjugate is captured at the control line via the interaction of anti-mouse IgG and the monoclonal anti-HAV antibody, two visible lines will be seen (see FIG. 8). Where the test result is negative for the presence of IgM anti-HAV, such that virus-conjugate and/or free conjugate is captured only at the control line via the interaction of anti-mouse IgG and the monoclonal anti-HAV antibody, one visible line will be seen (see FIG. 8). Actual results for two positive samples and one negative sample are shown on the right (see FIG. 8).

Example 3

Performance Summary

HAV IgM Rapid Test

The HAV IgM Rapid Test is for the qualitative detection of IgM antibodies to Hepatitis A virus (HAV) in human serum. The HAV IgM Rapid Test can be used for the presumptive detection of acute Hepatitis A infection. This HAV IgM Rapid Test should be used for patients with signs and symptoms that are consistent with Hepatitis A virus infection.

Device Description

Serum antibodies of the IgM class, when present, bind to anti-human IgM immobilised in a line across the test strip. Colloidal gold-labelled anti-HAV monoclonal forms complexes with the HAV antigen that is captured by HAV specific IgM in the patient's serum. These complexes are visualised as pink/purple line(s).

The performance of the test with serum from patients diagnosed with Acute Hepatitis A infection was investigated to determine the utility of this test for the rapid diagnosis of HAV infection.

An in-house evaluation was conducted to assess the sensitivity of the HAV IgM Rapid Test. The rapid test was performed on 43 sera consisting of a commercially available anti-Hepatitis A Mixed Titre Performance Panel (Boston Biomedical Inc, USA) and Acute Hepatitis A positive serum. All samples obtained by the Alfred Hospital were retested by ELISA (ETI-HAV-IgmK plus Cat No. NO142, Diasorin, Italy) at Select Vaccines to confirm HAV IgM status. A summary of rapid test results are presented below in Table 1.

The rapid test was able to detect 42 out of 43 HAV positive sera. The sample negative on the HAV IgM rapid, returned low positive results in 4 out of 6 commercial immunoassays with values just above the cut-off The sample tested negative for the remaining 2 Immunoassays.

TABLE 1

| Analysis of Acute HAV Sera | | | |
|---|---|---|---|
| | No. IgM + ve | No. IgM − ve | No. IgM + ve/ Total No (%) |
| HAV IgM ELISA Positive | 42 | 2 | 42/4443 (97.67%) |

Diagnostic Specificity

The performance of the test with serum from Australian blood donors was assessed to determine the specificity of the assay. One hundred and twenty two blood donor samples were obtained and HAV IgM status for each sample was confirmed by ELISA (ETI-HAV-IgmK plus Cat No. NO142, Diasorin, Italy). The ELISA and rapid test was performed on all samples and results are summarised in Table 2 below.

TABLE 2

| Analysis of HAV negative Sera | | | |
|---|---|---|---|
| | No. IgM − ye | No. IgM + ve | No. IgM − ve/ Total No (%) |
| HAV IgM ELISA Negative | 120 | 1 | 121/12 (99.18%) |

Cross-Reactivity

A panel of 136 specimens from patients with confirmed diseases other than Hepatitis A was tested to establish the analytical specificity of the HAV IgM Rapid Test. To evaluate the specificity of the HAV IgM Rapid Test, samples from patients with Cytomegalovirus (n=20), Epstein-Barr virus IgM (n=20), Epstein-Barr virus IgG (n=8), Rubella IgM (n=6), Measles IgM (n=8), Mumps IgM (n=7), Rheumatoid Factor (n=30) were used. In addition, serological cross-reactivity across the Hepatitis group was also assessed. Table 3 below provides a summary of the results.

TABLE 3

Cross Reactivity Data-HAV IgM Rapid Test

| Serum | No. IgM Negative/Total |
|---|---|
| Cytomegalovirus | 20/20 |
| EBV IgM | 18/20 |
| EBV IgG (EBNA) | 8/8 |
| Rubella IgM | 6/6 |
| Measles IgM | 8/8 |
| Mumps IgM | 7/7 |
| Hepatitis B | 6/7 |
| Hepatitis E | 19/20 |
| Hepatitis C | 10/10 |
| Rheumatoid factor (RF) | 30/30* |
| Total | 132/136 (97.06%) |

The results indicate that the "overall" specificity, considering factors such as the mix between blood donors and potentially cross reactive sera, is 252/257, i.e. 98.05%.

Example 4

The Utility of Adhesive Peptides Conjugated to Other Macromolecules Via Chemical Conjugation As a further example of the utility of the adhesive peptides in enhancing the binding of macromolecules to solid substrates, the adhesive peptide having the sequence WGWQWGPW (SEQ ID NO:1) or a derivative thereof having the sequence of $X_{aa1}\ A_1\ X_{aa2}\ A_2\ X_{aa3}\ A_3\ X_{aa4}\ X_{aa5}\ A_4$, (SEQ ID NO:2) or a part thereof wherein $X_{aa}$=any amino acid; and $A_1$ to $A_4$ is independently selected from a hydrophobic amino acid selected from; Ala, Gly, Ile, Phe, Pro, Met, Trp, Tyr, Val; D or L isomers thereof; and a functional analog thereof as substituted with a non-polar substituent such as, for example, an alkyl, alkenyl, alkynyl, aryl or heterocyclyl substituent; or a functional derivative thereof comprising at least about 20% amino acid sequence similarity thereto as disclosed in International Publication No. WO 2006/056009, which is incorporated herein in its entirety by reference, was prepared.

The peptide was prepared as an N-Hydroxysuccinimide (NHS) active ester, and conjugated to monoclonal antibody (MAb) K2-4F2 (antibody to hepatitis A virus) or MAb PH-315 (antibody to human IgM) by mixing at 4° C. for two days.

Figure 9:
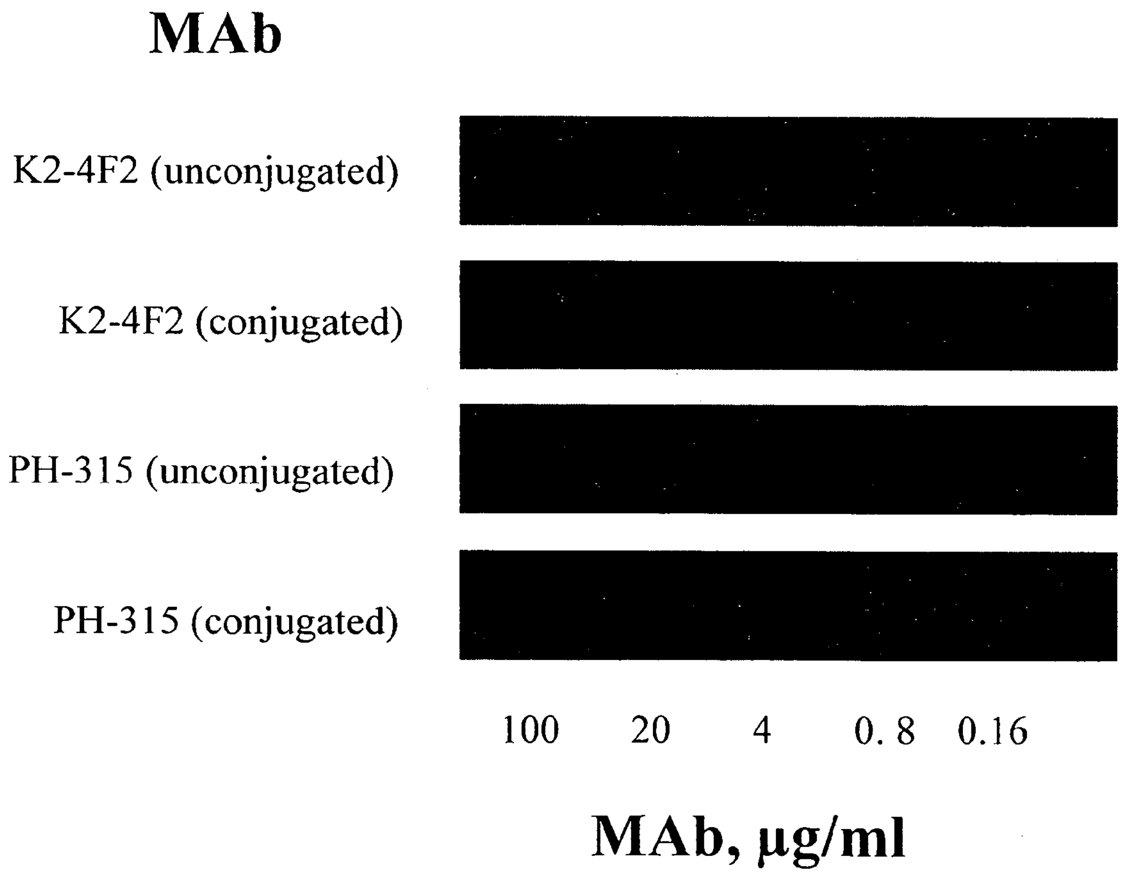
FIG. 9 is a photographic representation of data showing the utility of the adhesive peptides in enhancing the binding of macromolecules to solid substrates. The adhesive peptide WGWQWGPW was prepared as an N-Hydroxysuccinimide (NHS) active ester, and conjugated to monoclonal antibody (MAb) K2-4F2 (antibody to hepatitis A virus) or MAb PH-315 (antibody to human IgM) by mixing at 4° C. for two days. Serial dilutions of the adhesive peptide-conjugated MAbs were prepared in PBS, pH 7.4, and serial dilutions of the equivalent unconjugated MAbs were prepared in 0.1 M sodium bicarbonate buffer, pH 9.6. One hundred microlitres of each dilution was added to wells of Porex polyethylene membrane using a Bio DotBlot apparatus (BioRad). The amount of bound MAb was detected by probing with Alexa 680-conjugated anti-mouse IgG and exposure to the Odyssey infrared scanner (LiCor Inc.). Binding of the unconjugated MAbs to Porex membrane was inefficient, requiring 20 μg/ml of each MAb to yield a strong fluorescent signal. Conjugation of the MAbs to adhesive peptide resulted in an approximate 5-fold increase in the total amount of binding, requiring only 4 μg/ml of each MAb to yield a strong fluorescent signal, equivalent to that seen with 20 μg/ml of unconjugated MAb.

Serial dilutions of the adhesive peptide-conjugated MAbs were prepared in PBS, pH 7.4, and serial dilutions of the equivalent unconjugated MAbs were prepared in 0.1 M sodium bicarbonate buffer, pH 9.6. One hundred microlitres of each dilution was added to wells of Porex polyethylene membrane using a Bio DotBlot apparatus (BioRad). The amount of bound MAb was detected by probing with Alexa 680-conjugated anti-mouse IgG and exposure to the Odyssey infrared scanner (LiCor Inc.). The results are represented in FIG. 9.

Binding of the unconjugated MAbs to Porex membrane was inefficient, requiring 20 μg/ml of each MAb to yield a strong fluorescent signal. Conjugation of the MAbs to adhesive peptide resulted in an approximate 5-fold increase in the total amount of binding, requiring only 4 μg/ml of each MAb to yield a strong fluorescent signal, equivalent to that seen with 20 μg/ml of unconjugated MAb.

The following references, which are incorporated herein in their entireties, are cited herein to assist one skilled in the art in practicing the invention:

Bishop et al., *J. Virol. Methods,* 47:203-116, 1994.
Burton et al., *Proc. Natl. Acad. Sci. U.S.A.,* 88:10134, 1991.
Chaudhary et al., *Proc. Natl. Acad. Sci. U.S.A.,* 87:1066-1070, 1990.
Clackson et al., *Nature,* 352:624, 1991.
Craik C. S., *Science,* 228:291-297, 1985.
Cronin et al., *Biochem.,* 27: 4572-4579, 1988.
Gerit J. A., *Chem. Rev.,* 87:1079-1105, 1987.
Harlow and Lane, "*Antibodies: A Laboratory Manual*" Cold Spring Harbor Laboratory, 1988.
Hoogenboom et al., *Nucleic Acids Res.,* 19:4133, 1991.
Huston et al., *Proc. Natl. Acad Sci U.S.A.,* 85:5879-5883, 1988.
Kang et al., *Proc. Natl. Acad. Sci. U.S.A.,* 88:4363, 1991.

Kohler and Milstein, *European Journal of Immunology,* 6:511-519, 1976.

Knowles J. R., *Science,* 236:1252-1258, 1987.

Leatherbarrow R., *J. Prot. Eng.,* 1:7-16, 1986.

Lowman et al., *Biochemistry,* 30:10832, 1991.

MacGregor et al., *J. Clin. Microbiol.,* 18(5):1237-1243, 1983.

Sambrook, *Molecular Cloning: A Laboratoy Manual,* 3rd Edition, CSHLP, CSH, NY, 2001.

Shaw W. V., *Biochem. J.,* 246:1-17, 1987

Watson, J. D. et al., "*Molecular Biology of the Gene*", Fourth Edition, Benjamin/Cummings, Menlo Park, Calif., 1987.

Wild D. "*The Immunoassay Handbook*" Nature Publishing Group, 2001.

Wilks et al., *Science,* 242:1541-1544, 1988.

Reference to any "prior art" in this specification is not, and should not be taken as, an acknowledgement or any form of suggestion that this prior art forms part of the common general knowledge in any country.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features. Each embodiment described herein is be applied mutatis mutandis to each and every other embodiment unless specifically stated otherwise.

What is claimed is:

1. A kit for diagnosing or monitoring an infection with a virus by detecting the presence of an IgM antibody to the virus in a test sample from a subject, wherein the kit comprises:

a) an immunographic device comprising a porous membrane operably connected to a sample portion, a test portion comprising an IgM antibody binding agent, and optionally a control portion; and further comprising a sucker portion, a virus portion and a conjugate portion; and b) instructions for using the immunographic device to detect the presence of the antibody to the virus in the test sample.

2. A kit of claim 1 wherein the virus portion comprises a viral particle of the virus and the conjugate portion comprises a detection marker.

3. The kit of claim 2 wherein the IgM antibody binding agent is an antibody or an antibody binding fragment thereof.

4. The kit of claim 3 wherein the antibody or fragment is an anti-species antibody or antigen binding fragment thereof.

5. The kit of claim 3 wherein the antibody or fragment binds to the IgM antibody.

6. The kit of claim 2 wherein the detection marker comprises a visually detectable reporter molecule.

7. The kit of claim 6 wherein the detection marker is selected from a colloidal metal, colloidal metal oxide particle, colloidal non-metal particle, a dye and/or coloured latex.

8. The kit of claim 2, 6 or 7 wherein the detection marker is directly or indirectly bound to a virus binding agent.

9. The kit of claim 8 wherein the virus binding agent is an antibody or antigen binding fragment thereof that binds to the viral particle.

10. The kit of claim 9 wherein the antibody or fragment in the conjugate portion and the antibody to the virus in the sample recognize the same epitope on the viral particle.

11. The kit of claim 2 wherein the viral particle is a hepatitis A virus (HAV) viral particle.

12. The kit of claim 9 wherein the antibody or fragment in the conjugate portion is an anti-HAV antibody.

13. The kit of claim 10 wherein the epitope is an immunodominant epitope.

14. The kit of claim 2 wherein the antibody binding agent is bound to the test portion of the device using an adhesive peptide having the sequence WGWQWGPW (SEQ ID NO:1).

15. The kit of claim 14 wherein the antibody binding agent is conjugated to the adhesive peptide.

16. The kit of claim 2 wherein the viral particle in the virus portion is an inactivated viral particle.

17. The kit of claim 1 wherein the sucker portion, virus portion and conjugate portion are adapted to be operably connected to the porous membrane before use and/or when in use.

18. The kit of claim 11 wherein the antibody or fragment in the conjugate portion is an anti-HAV antibody.

19. The kit of claim 1 wherein the virus is a hepatitis A virus viral particle, a hepatitis B viral particle, a hepatitis C viral particle, a hepatitis D viral particle or a hepatitis E viral particle.

* * * * *